United States Patent
Carretero Batista et al.

(10) Patent No.: US 9,608,563 B2
(45) Date of Patent: Mar. 28, 2017

(54) METHOD FOR DETECTING THE DEGREE OF SOILING OF PV MODULES

(71) Applicant: skytron energy GmbH, Berlin (DE)

(72) Inventors: Agustin Javier Carretero Batista, Berlin (DE); Hendrik Hoffmann, Zeuthen (DE)

(73) Assignee: SKYTRON ENERGY GMBH, Berlin (DE)

(*) Notice: Subject to any disclaimer, the term of this patent is extended or adjusted under 35 U.S.C. 154(b) by 57 days.

(21) Appl. No.: 14/722,686

(22) Filed: May 27, 2015

(65) Prior Publication Data

US 2015/0346123 A1 Dec. 3, 2015

(30) Foreign Application Priority Data

May 27, 2014 (DE) .................. 10 2014 107 417

(51) Int. Cl.
| | |
|---|---|
| *G01R 31/26* | (2014.01) |
| *G01N 27/00* | (2006.01) |
| *H02S 50/10* | (2014.01) |
| *G01R 21/06* | (2006.01) |
| *G01R 21/00* | (2006.01) |
| *H02S 50/00* | (2014.01) |

(52) U.S. Cl.
CPC .............. *H02S 50/10* (2014.12); *G01N 27/00* (2013.01); *G01R 21/00* (2013.01); *G01R 21/06* (2013.01); *H02S 50/00* (2013.01)

(58) Field of Classification Search
CPC ......... H02S 50/10; H02S 50/00; G01R 21/06; G01R 21/00; G01N 27/00
USPC .................. 324/761.01, 71.1; 702/61, 58
See application file for complete search history.

(56) References Cited

U.S. PATENT DOCUMENTS

| | | | |
|---|---|---|---|
| 8,300,439 B2 * | 10/2012 | Little ................ | G01D 9/005 307/82 |
| 8,725,437 B2 | 5/2014 | Caine | |
| 2012/0053867 A1 * | 3/2012 | Dunn .................. | H02S 50/10 702/58 |

FOREIGN PATENT DOCUMENTS

EP 2034323 A2 3/2009

* cited by examiner

*Primary Examiner* — Amy He
(74) *Attorney, Agent, or Firm* — MacMillan, Sobanski & Todd, LLC

(57) ABSTRACT

A method for detecting the degree of soiling of PV modules of a string includes the following steps: determination of the deviations of the string power output values from a calculated reference value over the last year; calculation of a historical trend line from the deviations; determination of a maximum difference between the trend line and the deviations; calculation of final deviations of the power output values through subtraction of the maximum difference from the trend line; and determination of the degree of soiling through subtraction of the final deviations from the deviations.

12 Claims, 8 Drawing Sheets

METHOD FOR DETECTING THE DEGREE OF SOILING OF PV MODULES

CROSS-REFERENCE TO RELATED APPLICATIONS

This application claims priority to German Patent Application No. DE 10 2014 107 417.3 filed May 27, 2014, the disclosures of which are incorporated herein by reference in entirety.

BACKGROUND OF THE INVENTION

The invention relates to a method for detecting the degree of soiling of PV modules.

The soiling of PV modules reduces their efficiency and thus their electrical output at a given level of solar radiation. It can therefore be of interest to clean the photovoltaic modules or to take the soiling into account for prognoses of the PV system. In both cases, it is helpful to know the degree of soiling.

BRIEF SUMMARY OF THE INVENTION

It is a feature of the invention to improve the detection of the degree of soiling of PV modules.

This feature is achieved by the features of the independent claim. Advantageous developments of the invention are defined in the dependent claims.

According to the invention, a method for detecting the degree of soiling of PV modules of a string comprises the following steps:
  Determination of the deviations of the string power output values from a calculated reference value over the last year;
  Calculation of a historical trend line from the deviations;
  Determination of a maximum difference between the trend line and the deviations;
  Calculation of final deviations of the power output values through subtraction of the maximum difference from the trend line; and
  Determination of the degree of soiling through subtraction of the final deviations from the deviations.

The method according to the invention is based on the determination of the deviations of the string power output values from a calculated reference value or calculated reference values. Since the PV modules and their string power outputs are used directly and not additional measuring devices, the method is very precise and independent of module or sensor technologies. What is more, the string monitoring data are easily available, precise and in high temporal resolution. Using the detected degree of soiling, cleaning cycles can be established, which is advantageous particularly in regions in which water is scarce, since the water required for cleaning can thus be limited to a minimum.

The method can be based on daily values. This means that the determination of the rate of soiling has a resolution of one day. The underlying measured values, such as the string power output, for example, can have a lower resolution, for example one minute. The resolution of one day is sufficient and enables a determination of the rate of soiling after a lapsed day or after sunset if no other measured values need to be further processed.

An irradiation sensor can be used for the calculation of the string power output values. Using the sensor, the power output calculation and/or the calculation of the reference value can be reconciled, which increases the reliability of the method.

A temporal mismatch of the string power output values as a result of alignment errors of the irradiation sensor can be detected and taken into account. This calibration increases the accuracy of the method.

Measurement errors resulting from the ageing of the irradiation sensor can be detected and taken into account by comparing all previously observed cloud-free days. With this step, the drift occurring as a result of ageing can be detected and calibrated so that no corruption of the measured results occurs.

String power output values can be used from a time interval of one hour around the maximum elevation angle of the Sun. In this time interval, the values are stable and reliable due to the high level of radiation.

The string power output values can be discarded if an output power value of an inverter of the string exceeds a threshold, the threshold being greater than 95 percent and less than 100 percent of a rated output power of the inverter. In this way, so-called inverter clipping is eliminated in which the inverter is operated above or at the boundary of its rating, which can lead to unstable operating conditions unsuitable for the method due to poor accuracy. The discarding can be done by not observing that day for the determination of the module soiling.

The string power output values can be discarded if an average measured radiation deviates from a simulated radiation by a threshold value, the threshold lying between 5 percent and 25 percent. Here, days are filtered out on which the solar radiation is not sufficiently high for a reliable and accurate method.

The string power output values can be discarded if a deviation between two temporally successive measured values of the radiation exceeds a threshold, the threshold lying between 100 Watt per square meter and 300 W per square meter. Here, days are filtered out on which the solar radiation is not sufficiently high for a reliable and accurate method.

The string power output values can be discarded if an output power of an inverter of the string has been limited, for example, by a defect or a throttling. The accuracy is reduced in these cases, so these values or the time periods for these values are not used.

The overall operating time of the PV modules can be observed, i.e., from startup to the current point in time. This offers the advantage that the method becomes more precise due to the improved available data.

The degree of soiling of at least one string can be determined. In relation to the PV system, i.e., the regenerative power station, certain parts based on individual strings or the entire power station based on all strings can thus be observed.

Other advantages of this invention will become apparent to those skilled in the art from the following detailed description of the preferred embodiments, when read in light of the accompanying drawings.

DETAILED DESCRIPTION OF THE INVENTION

The drawings are merely intended to explain the invention and do not limit it. The drawings and the individual parts are not necessarily to scale. Same reference symbols refer to same or similar parts.

Figure 1:
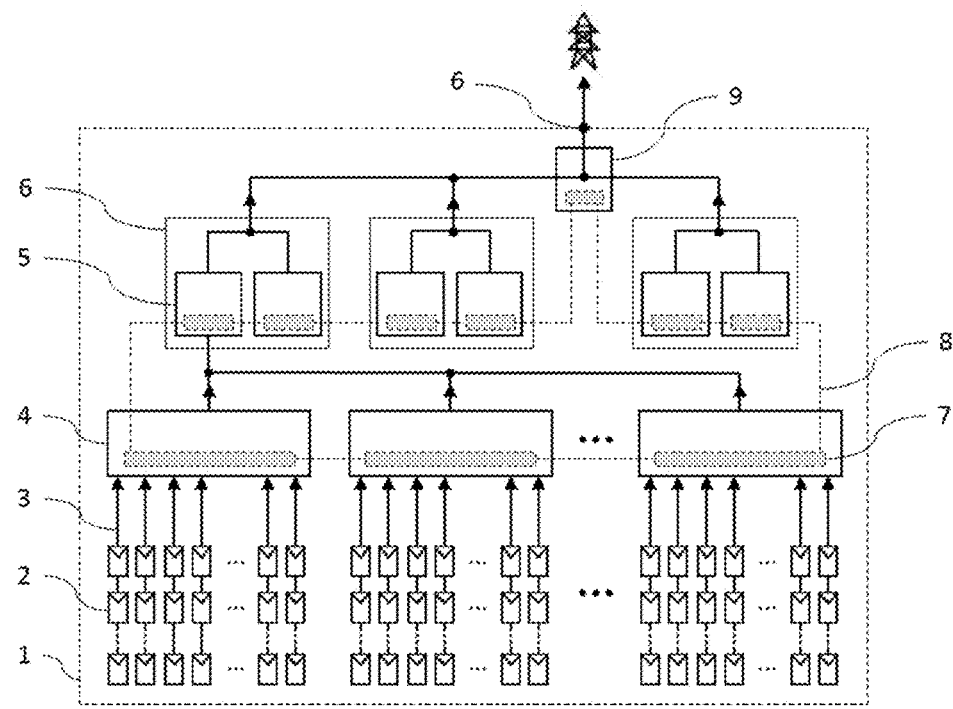
FIG. 1 shows a schematic view of a PV power station.

FIG. 1 shows a photovoltaic power station 1 with several solar modules 2. The solar modules 2 are arranged in strands or strings 3. Several solar modules 2 are connected in series for this purpose. Several strings 3 can be grouped together logically and/or by circuit engineering into zones.

Each string 3 leads to a generator connection box 4 or a similar connection point for the string 3. Here, a string 3 is associated with each generator connection box 4, it also being possible for several strings 3 to be connected to a generator connection box 4. The generator connection box 4 need not be an independent unit but can also be a component, such as a printed circuit board, assembly or software routine for signal processing, of another electrical and/or electronic unit.

The generator connection boxes 4 are connected to alternating-current converters or power converters 5. The alternating-current converters 5 convert the direct current generated by the solar modules 2 into alternating current. Here, two generator connection boxes 4 are connected to one alternating-current converter 5. This ratio can be altered depending on the system, the components used, etc.

The alternating-current converters 5 are grouped together into a power station block 6 and/or connected to a mains interconnection point 6. The mains interconnection point 6 is connected on the output side to the mains or grid.

The connections outlined above between the solar modules 2, the generator connection boxes 4, the alternating-current converters 5 and/or the mains interconnection point 6 are first and foremost connections for transferring power. Moreover, information can be transferred via these connections and/or other connections. This information can be explicit information such as control data, operating data, etc. or implicit information that is contained in the power transfer and extracted.

A control or arithmetic unit 7 picks up measured values of the measuring channels 3 auf. The measured values are fed to the control unit 7 via signal lines 8. FIG. 1 shows several signal lines to the solar modules 2, the generator connection boxes 4, the alternating-current converters 5 and the mains interconnection point 6. Other signal lines to the other solar modules 2, generator connection boxes 4 and the alternating-current converter 5 are not shown for the sake of clarity. It is also possible to use only one type of signal line 8, for example to the generator connection boxes 4.

String power output values of the individual strings are detected in the generator connection boxes 4 and/or the alternating-current converters 5. The string power output values characterize the electrical power generated per string, particularly the active power. The string power output values are measured regularly, for example at a clock frequency of one minute or of a few minutes, such as five or ten minutes, for example.

The control unit 7 processes and validates the measured values as a function of the position of the Sun. A power station control or regulator 9, which monitors and controls operational sequences of the photovoltaic power station 1, is connected to the control unit 7, so that measured values, information, results and other data can be exchanged. The control unit 7 can be embodied as a component of the power station control 9 in hardware and/or software.

The method described below for detecting the degree of soiling of PV modules 2 of a string 3 is carried out in the control unit 7 and/or the power station control 9. The method can also be carried out by another unit that is spatially separated from the photovoltaic power station 1, for example. The measured values are then transferred via wired and/or wireless connections from the photovoltaic power station 1 to the unit.

In the following, the method for detecting the degree of soiling of PV modules 2 of a string 3 is described in further detail.

The method is based on the calculation or determination of the deviations of the string power output values from a calculated reference value or calculated reference values. The measured string power output is based on accurate current and voltage measurements that are carried out every minute. The normalization of the standardized STC power output under the measured weather conditions is used for the calculated or simulated reference values. Data or measured values of the irradiation sensor are validated or compensated before being used. This can include a compensation of a misalignment and/or deviations as a result of ageing. The calculation of the final rate of soiling is only performed under suitable environmental conditions within the operating limits of the inverter MPP operation. A precise time filter algorithm is then applied in order to position the optimal time window for the calculation within selected clear days.

Figure 2:
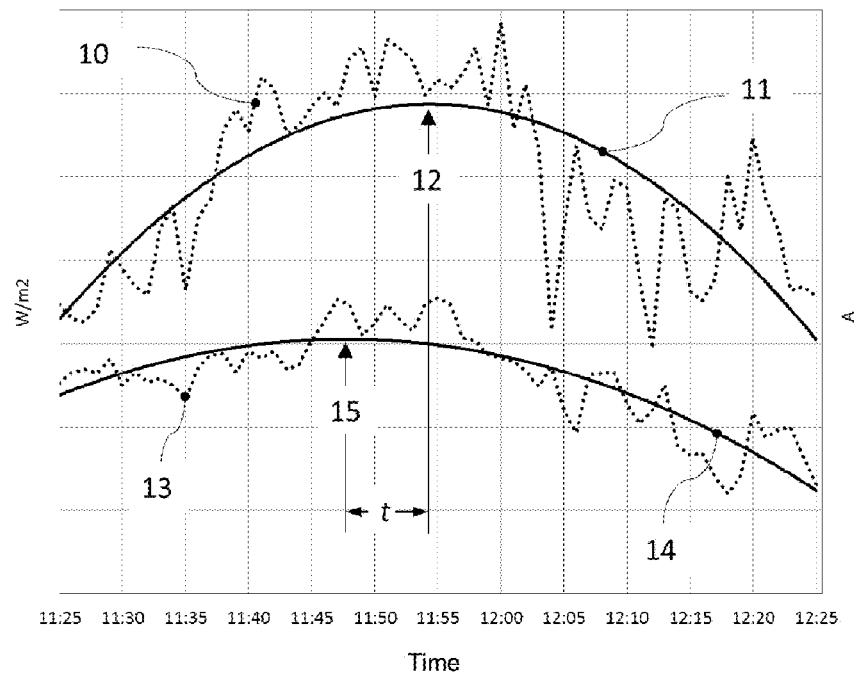
FIG. 2 shows a diagram for detecting a temporal mismatch of the string power output values resulting from alignment errors of an irradiation sensor.

First, a temporal mismatch of the string power output values is detected through alignment errors of an irradiation sensor. This is described on the basis of FIG. 2. FIG. 2 is a combined illustration of the radiation in W/m$^2$ and the string current in A plotted over a time period of one hour around midday.

An approximation polynomial 11 with a maximum radiation 12 at about 11:54 is calculated from a curve of the radiation 10. An approximation polynomial 14 with a maximum current 15 at about 11:47 is calculated from a curve of the string current 13. The two maximums are offset from each other by a time span t, which is seven minutes in this case. This time span or duration is based on a horizontal misalignment of the sensor.

The following formula describes the delay:

$$\text{Delay}_{SENSOR} \text{ [minutes]} = \text{Time}_{MAX.\ RADIATION} - \text{Time}_{MAX.\ STRING\ CURRENT}$$

where $Delay_{sensor}$ is the delay, $Time_{Max.\ Radiation}$ is the point in time of maximum radiation and $Time_{Max.\ String\ Current}$ is the point in time of the maximum string current.

Figure 3:
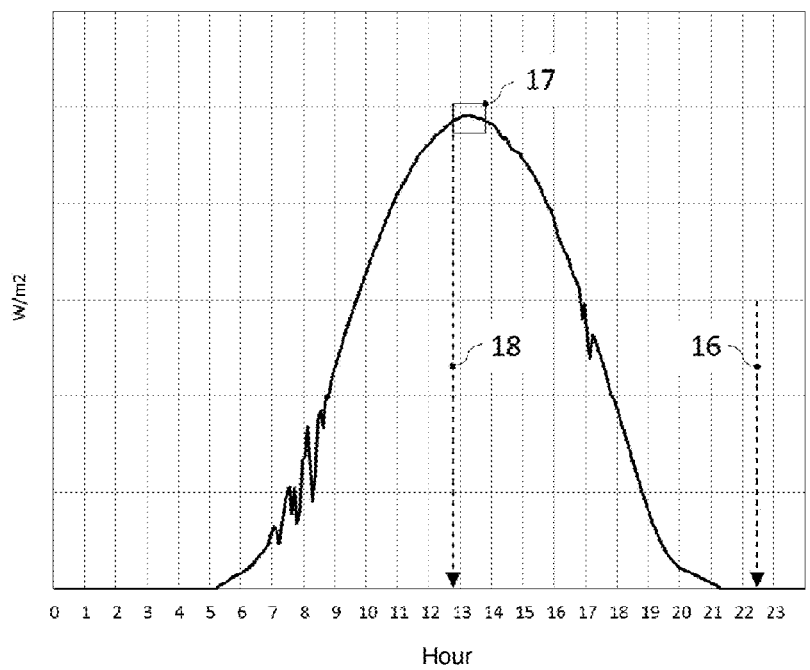
FIG. 3 shows a diagram of a temporal representation of the method.

FIG. 3 shows the time sequence of the method. The radiation in W/m² is plotted over the day, i.e., from zero to twenty-four hours. Each day, a check is made after sunset whether that day meets the conditions described below for being used for the calculation of the deviation of the string power output and of the string power output values.

The check is performed at a point in time 16, here 22:30, which corresponds to the local time of the power station 1. This corresponds to the following formula.

$$Checking\ Time_{CLEAR-SKY\ DAY}=22:30:00\ (Local\ Time)$$

where $Checking\ Time_{Clear-Sky\ Day}$ corresponds to the checking time for a day with a clear sky.

FIG. 2 also shows a time interval 17 of, for example, one hour around the maximum elevation angle of the Sun for the detection and/or consideration of the measured values. Optimal radiation conditions are prevalent in this interval 17. The start time 18 for the time window or interval 17 is calculated based on the following formula, which takes the previously determined delay of the sensor into account.

$$Time_{NTW}^{start}=Time_{SOLAR\ NOON}+Delay_{SENSOR}-30\ minutes$$

where $Time_{start\ NTW}$ corresponds to the start time 18 of the interval 17 and $Time_{Solar\ Noon}$ corresponds to the maximum elevation angle of the Sun.

The checked day or day to be checked is discarded if the power station 1 or its output power has been limited or components of the power station 1 are defective. Only if the output power of the inverter 5 or of the inverters or of the power station 1 lie above a power output threshold having a size of over 90%, for example. The power output threshold should be as close as possible to the maximum possible value.

The checked day is also discarded if the inverter 5 of the string 3 approaches its rated output power. This has the consequence of an output power of an inverter 5 of the string 3 exceeding a threshold, upon which the string power output values of this string 3 or all measured values of the power station 1 are discarded. The threshold should preferably be less than 100 percent of a rated output power of the inverter 5. Preferably, the threshold is greater than 95 percent and less than 100 percent of a rated output power of the inverter 5. The following formula describes this criterion.

$$Power_{inverter}<Power_{inverter}^{nominal}*x$$

where $Power_{inverter}$ is the output power of the inverter 5, $Power_{Nominal\ inverter}$ is the rated output power of the inverter 5 and x is the threshold.

This effect, which is known as inverter clipping, occurs when the modules emit a higher power output than their indicated standardized power output STC. This power output is defined under normal conditions, for example for radiations over 1000 W/m² and module temperatures below 25° C.

Figure 4:
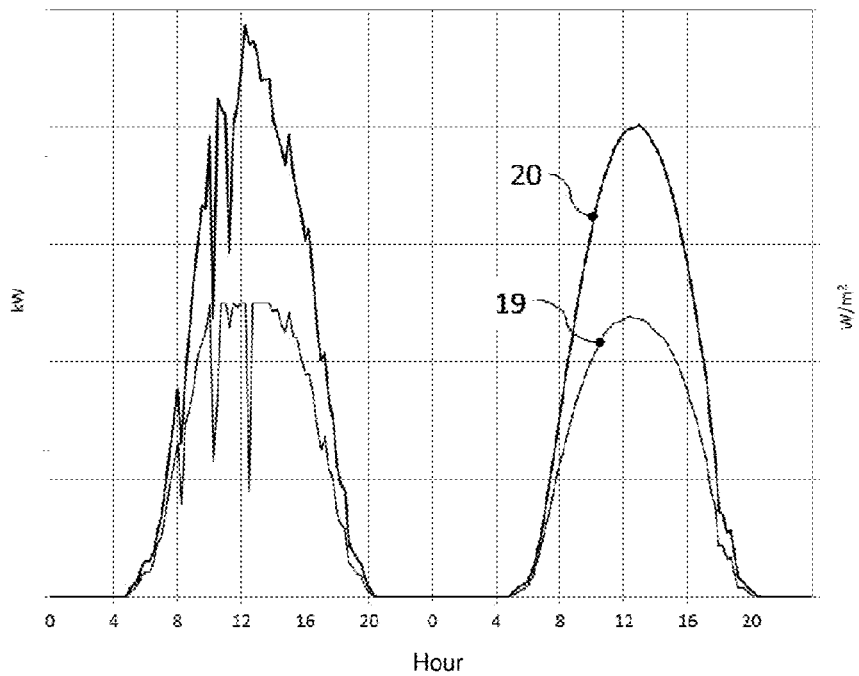
FIG. 4 shows a diagram illustrating an inverter clipping.

FIG. 4 illustrates an example. Shown there are a radiation curve 19 in W/m² and a power output curve 20 of the inverter 5 in kW. Visible to the left is a day with clipping or overmodulation of the power output curve 20 due to increased radiation. The day to the right with lower radiation shows a smooth power output curve 20. The day to the left is discarded, whereas the day to the right continues to be examined.

In a next step, the direct average measured radiation during a clear day at the maximum elevation angle of the Sun ($E_{t,max}$) is simulated. The intensity of the solar radiation over the Earth's atmosphere ($E_S$), the geographic width Φ of the power station 1, the tilt angle β of the module 2, the tilt angle of the Earth (δ) and the hour angle of the Sun (ω) are taken into account. The following formula describes the relation.

$$E_{t,max}=E_S*[\cos(\Phi-\beta)*\cos\delta*\cos\omega+\sin(\Phi-\beta)*\sin\delta]$$

Figure 5:
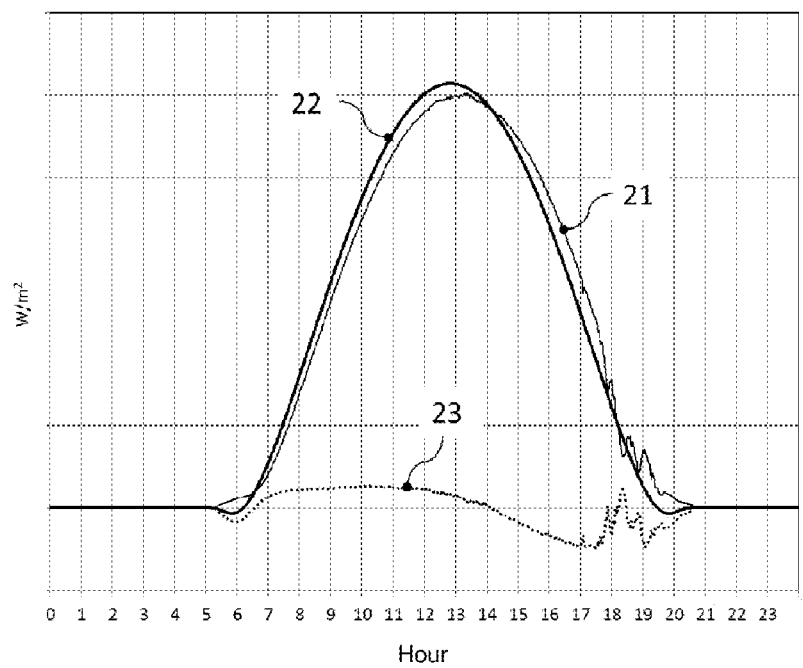
FIG. 5 shows a diagram of solar radiation of one day.

FIG. 5 shows an example of a radiation on a clear day. The radiation is plotted in W/m² over a day. The curve 21 represents the average measured radiation of a reference cell. The curve 22 shows the simulated radiation and the curve 23 indicates the difference between measured value and simulation.

The day or string power output values are discarded if the average measured radiation deviates from the simulated radiation by a threshold, the threshold lying between 5 percent and 25 percent. The checked day is this discarded if the solar radiation is insufficient.

Figure 6:
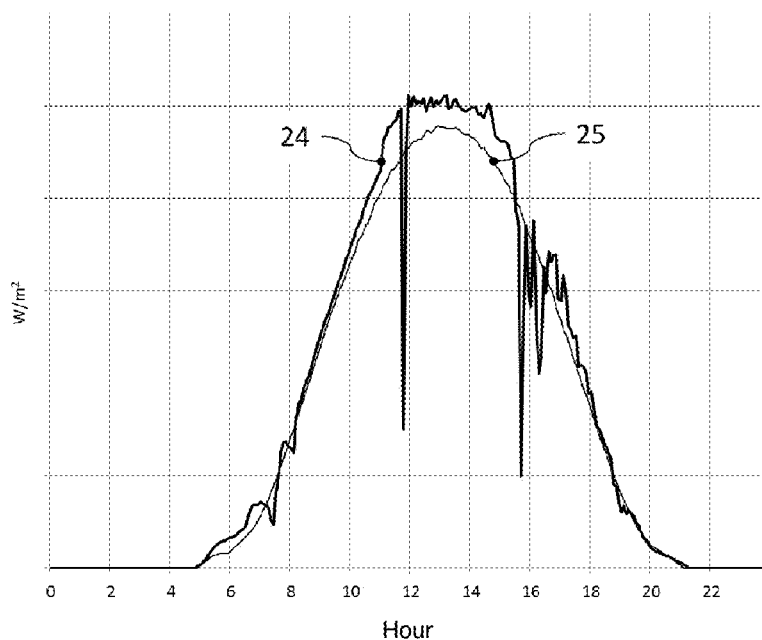
FIG. 6 shows a diagram for illustrating high and stable radiation.

The day is discarded if the solar radiation is not stable enough. This is shown in FIG. 6. There, the radiation values for two days are plotted against the hours of the day. The curve 24 of a cloudy day exhibits a discontinuous curve, whereas the curve 25 of a clear day exhibits a continuous curve that is well suited to further calculation.

According to the formula $$\sum_{i=1}^{60}|G_i-G_{i-1}|<y\ W/m^2$$

the sum of all absolute differences between the measured solar radiation $G_i$ in each minute of the midday time interval 17 and of the preceding minute $G_{i-1}$ should lie below a threshold y. The threshold y lies between 100 watts per square meter and 300 W per square meter.

If the checked day does not meet all or at least a certain selection of the above criteria or conditions, the day is discarded and the next day is observed, i.e., the search for a clear day is continued. Here, a clear day refers to a day that meets all or at least a certain selection of the above criteria.

If the day meets all of the criteria, a deviation of the string power output value is calculated or determined. This calculation is preferably performed every minute in the time interval 17.

If the inverter 5 is not at the MPP (Maximum Power Point), the corresponding minute is discarded. According to the formula $$I_{string}>1\ A$$

the measured string current should be more than 1 ampere.

Subsequently, the string active power is calculated as a product of the measured string current and the measured string voltage in the first minute of the interval 17 according to the following formula.

$$P_{MPP,real}=I_{string}*V_{string}$$

The rated string power output $P_{STC}$ is calculated as the product of the module STC output power $P_{Module\ STC}$, the number of serially connected modules n and the number of strings connected in parallel in a measuring channel p. This is indicated in the following formula.

$$P_{STC}=P_{STC}^{module}*n*p$$

Based on the rated string power output $P_{STC}$, the string power output is calculated at the measured module temperature $P_{Tmod\ STC}$ as follows.

$$P_{STC}^{Tmod} = P_{STC} * [1+\gamma*(T_{mod}-25°\ C.)]$$

where $T_{mod}$ is the measured module temperature and $\gamma$ is the temperature coefficient of the module output power ist.

Figure 7:
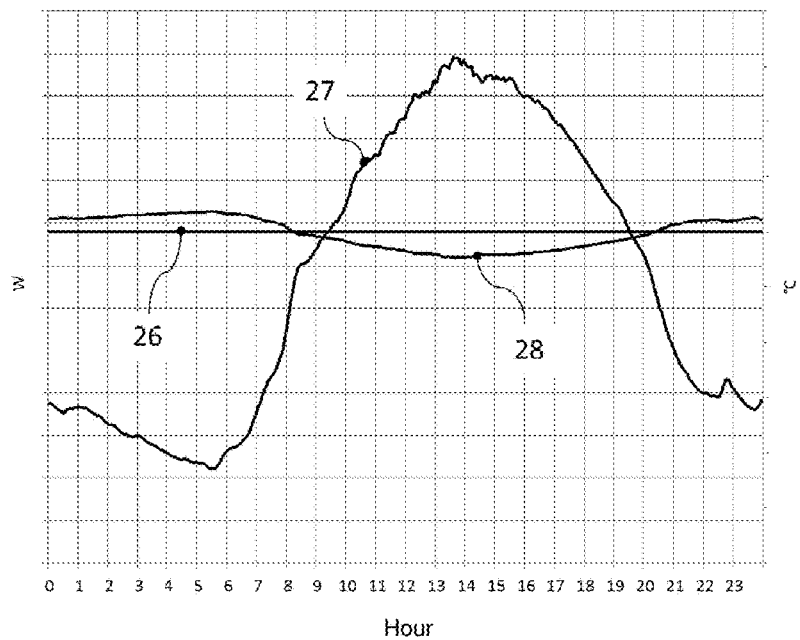
FIG. 7 shows a diagram illustrating a temperature normalization of the power output.

In FIG. 7, the curves are plotted in watts and ° C. against the hours of the day. The rated string power output $P_{STC}$ is represented as the curve 26 and the measured module temperature $T_{mod}$ is represented as the curve 27. The temperature-normalized string power output $P_{Tmod\ STC}$ is represented as the curve 28

The measured radiation $G_t$ is adapted through compensation with the average deviation of the sensor based on ageing. A calculated or simulated rate of 0.08335% per year is set. The compensated radiation $G_{t,\ comp}$ is thus calculated as:

$$G_{t,comp} = G_t * (1+0.08335*years)$$

The string power output under the measured radiation is simulated based on the temperature-normalized string power output $P_{Tmod\ STC}$ and in consideration of the compensated radiation $G_{t,comp}$. According to the following formula, the string power output is as follows under the measured radiation $P_{MPP,\ sim}$:

$$P_{MPP,sim} = P_{STC}^{Tmod} * \frac{G_{t,comp}}{1000\ W/m^2}$$

Figure 8:
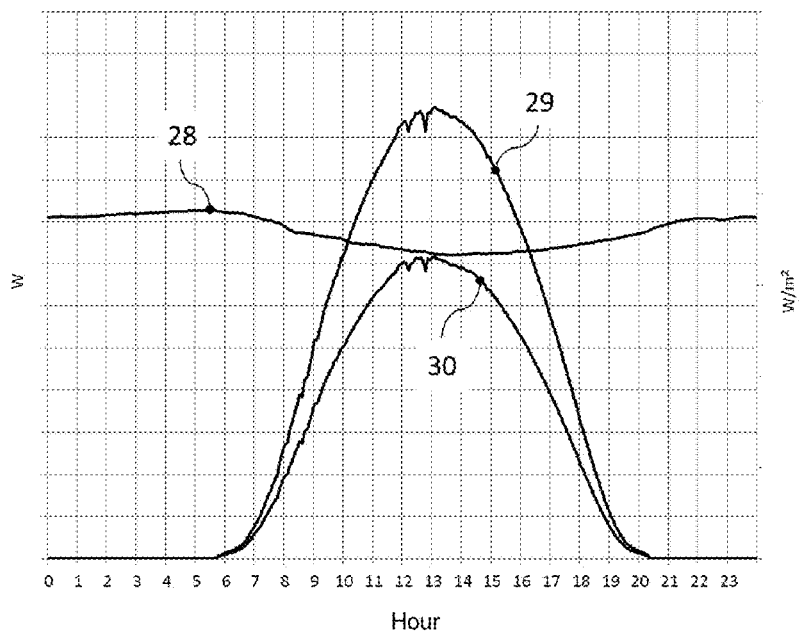
FIG. 8 shows a diagram illustrating a radiation normalization of the power output.

In FIG. 8, the power outputs are plotted in W and the radiation in W/m² against the hours of the day. Like in FIG. 7, the curve 28 shows the temperature-normalized string power output $P_{Tmod\ STC}$, and the curve 29 shows the compensated radiation $G_{t,comp}$. The resulting string power output under the measured radiation $P_{MPP,sim}$ is represented as the curve 30.

In another step, the deviation of the string power output Deviation_$P_{MPP}$ is calculated as the relationship between the string active power $P_{MPP,\ real}$ and the simulated string power output under the measured radiation $P_{MPP,\ sim}$ according to the following formula.

$$\text{Deviation\_P}_{MPP}[\%] = \left(1 - \frac{P_{MPP,real}}{P_{MPP,sim}}\right) * 100$$

Figure 9:
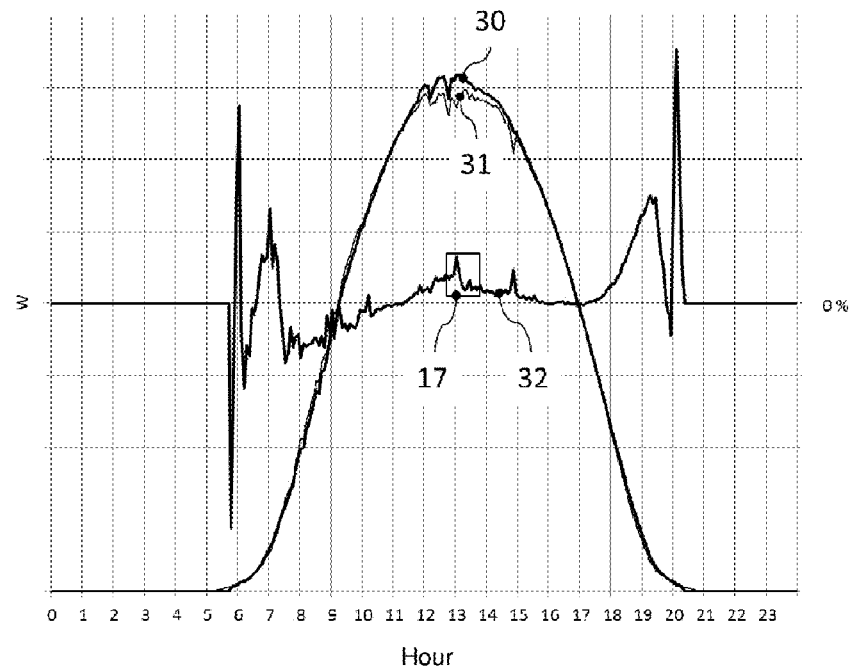
FIG. 9 shows a diagram illustrating the calculation of the power deviation.

The results are shown in FIG. 9, the string power output under the measured radiation $P_{MPP,sim}$ being represented as the curve 30 and the string active power $P_{MPP,real}$ as the curve 31. The deviation of the string power output Deviation_$P_{MPP}$ is represented in percent as the curve 32.

The average deviation of the string power output values Deviation_$P_{MPP,mean}$ within the interval 17 is calculated in consideration of the number of minutes n in which the inverter 5 runs in MPP. The following formula offers the basis of the calculation.

$$\text{Deviation\_P}_{MPP,mean}[\%] = \frac{\sum_{i=1}^{n} \text{Deviation\_P}_{MPP,i}}{n}$$

Figure 10:
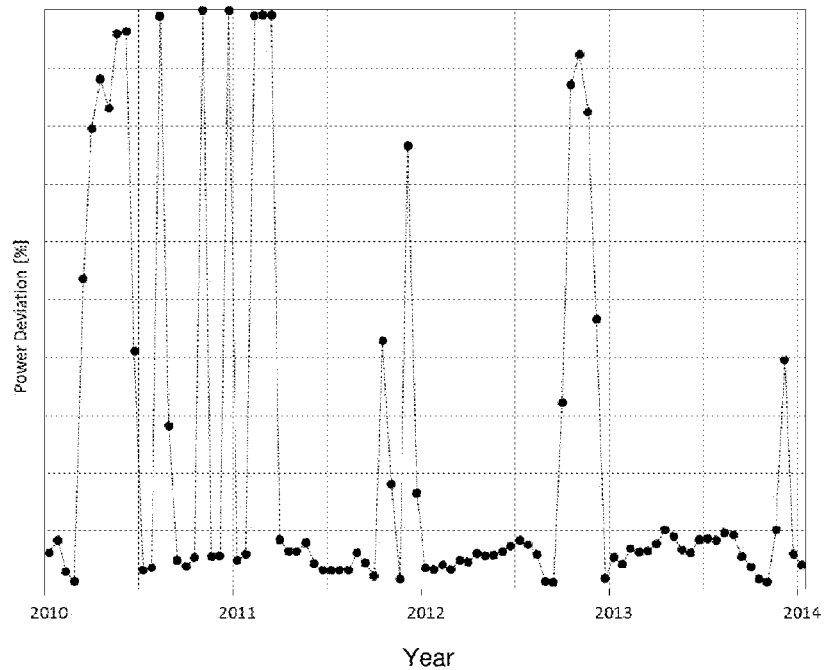
FIG. 10 shows a diagram of the historical deviation of the string power output.

For each accepted day, an average deviation of the string power output value Deviation_$P_{MPP,mean}$ is calculated and plotted over time together with all of the preceding values as shown in FIG. 10. It can be seen that several very high values or outliers are present. These values are caused by snow conditions or other interference and will need to be filtered out before continuing with the calculation.

Here, all of the values that lie above the zero value by a threshold z in percent are filtered out. Only low values are considered. The formula for this step is:

$$\text{Deviation\_P}_{MPP,mean} < y$$

Figure 11:
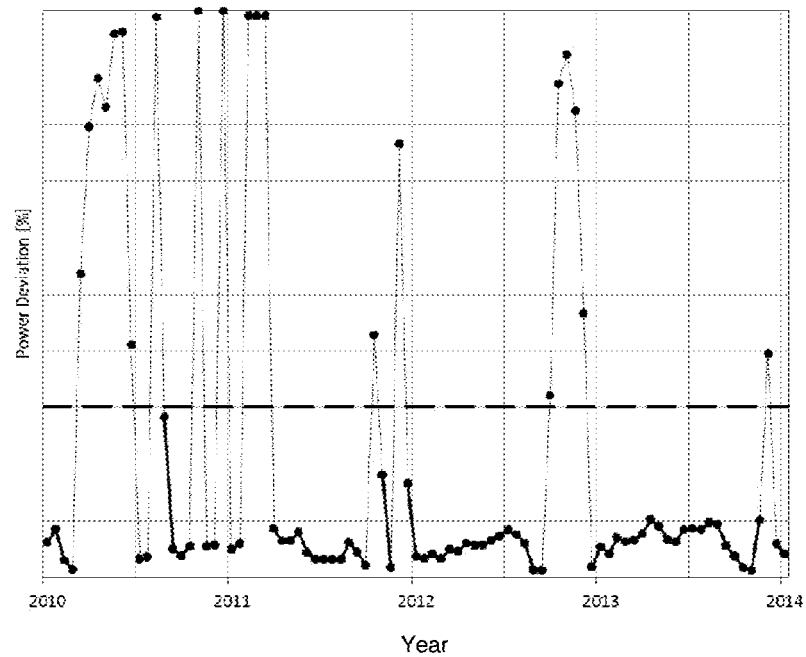
FIG. 11 shows a diagram of the historical deviation of the string power output after a first filtering.

The value of y can be set to the conditions of the power station, the measured values and/or the desired resolution or accuracy. Preferably, the value of y lies between 20 and 50 percent. The result of this filtering is shown in FIG. 11.

The average deviation μ and the standard deviation σ are calculated from the filtered values in consideration of the remaining clear days n according to the following formulas.

$$\mu = \frac{\sum_{i=1}^{n} \text{Deviation\_P}_{MPP,mean,i}}{n}$$

$$\sigma = \sqrt{\frac{\sum_{i=1}^{n} (\text{Deviation\_P}_{MPP,mean,i})^2}{n}}$$

Now all of the values above or greater than the standard deviation plus the average deviation according to the following formula are discarded.

$$\text{Deviation\_P}_{MPP,mean} < \mu + \sigma$$

Figure 12:
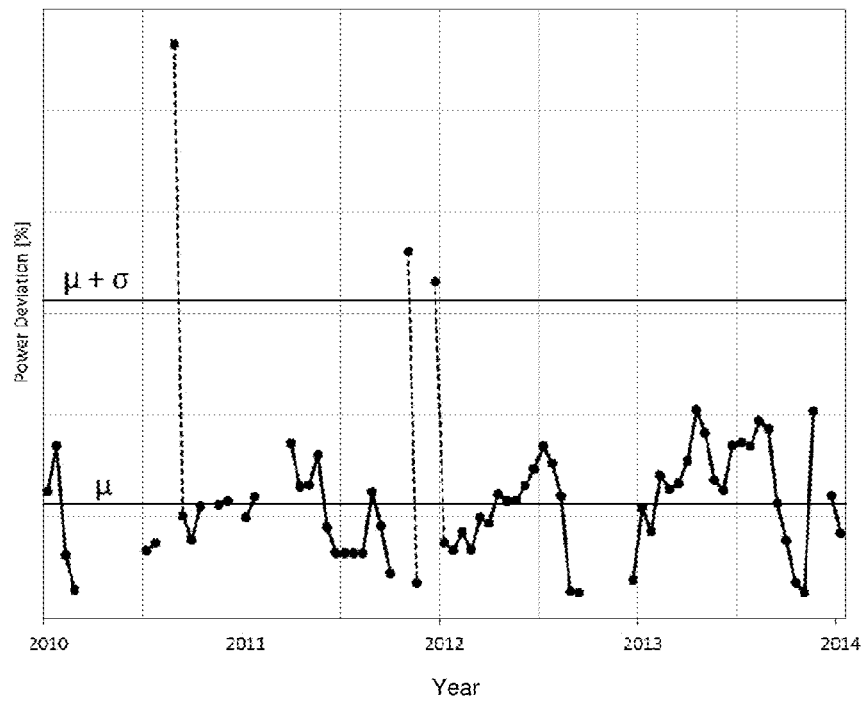
FIG. 12 shows a diagram of the historical deviation of the string power output after a second filtering.

As shown in FIG. 12, only the lower values are adopted.

A new deviation curve is calculated from the remaining values. For each remaining clear day, the average of the previous values is calculated only for the last year in consideration of the remaining clear days n within this time period.

$$\text{Deviation\_P}_{LAST\ YEAR}[\%] = \frac{\sum_{i=1}^{n} \text{Deviation\_P}_{MPP,mean,i}}{n}$$

Figure 13:
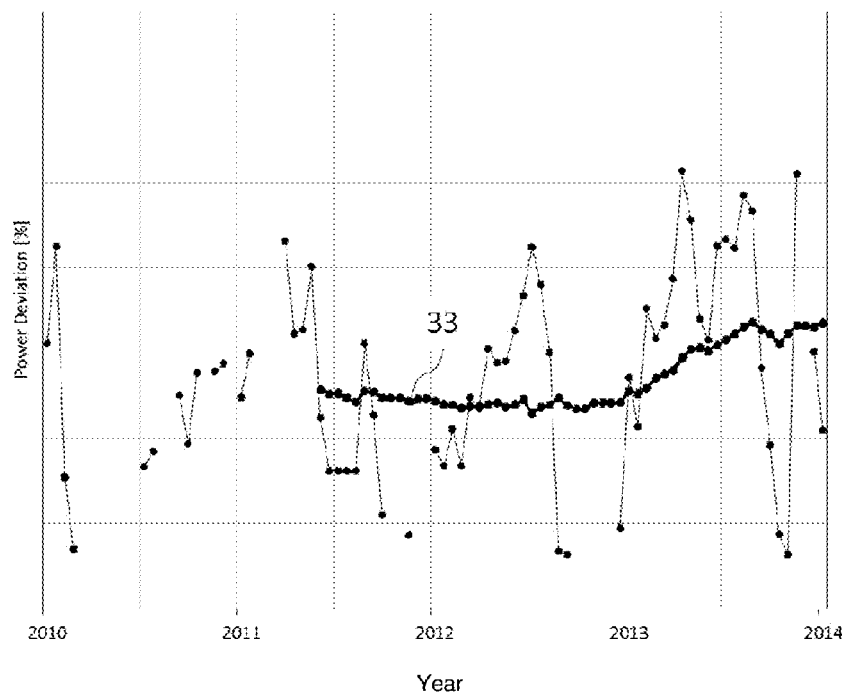
FIG. 13 shows a diagram of the historical deviation of the string power output with a last-year average.

In FIG. 13, the new deviation curve Deviation_$P_{LAST\ YEAR}$ is shown as the curve 33. A rising trend for this curve can be seen from FIG. 13.

Figure 14:
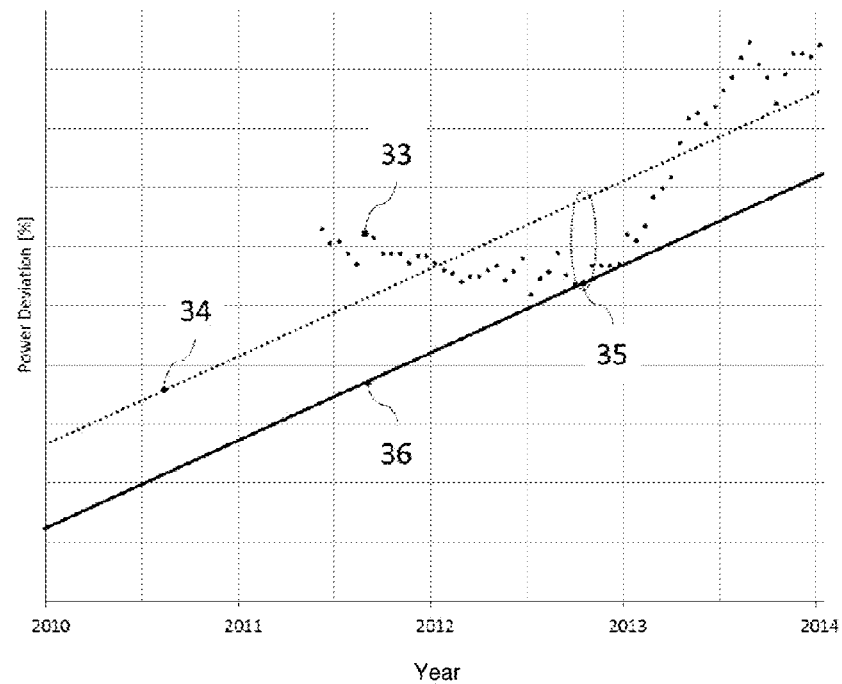
FIG. 14 shows a diagram of the last-year average of the deviation of the string power output with a trend line.

A historical trend line Deviation_$P_{TREND\ LINE}$ 34 is calculated from all average deviation values 33 of the last year. This trend line 34 is shown in FIG. 14.

A maximum difference 35 between the trend line 34 and the deviations 33 is calculated by comparison for each value of the trend line 34 with the corresponding deviation value 33. The maximum difference Difference$_{Max}$ calculated in this way is obtained using the following formula:

$$\text{Difference} = \text{Deviation\_P}_{TREND\ LINE} - \text{Deviation\_P}_{LAST\ YEAR}$$

The deviation of the module output power Deviation_$P_{Module}$ 36 is then calculated through subtraction of the maximum difference Difference$_{Max}$ 35 from the historical trend line Deviation_$P_{TREND\ LINE}$ 34. The following formula describes this.

$$\text{Deviation\_P}_{MODULE} = \text{Deviation\_P}_{TREND\ LINE} - \text{Difference}_{MAX}$$

The curves are shown in FIG. 14.

Figure 15:
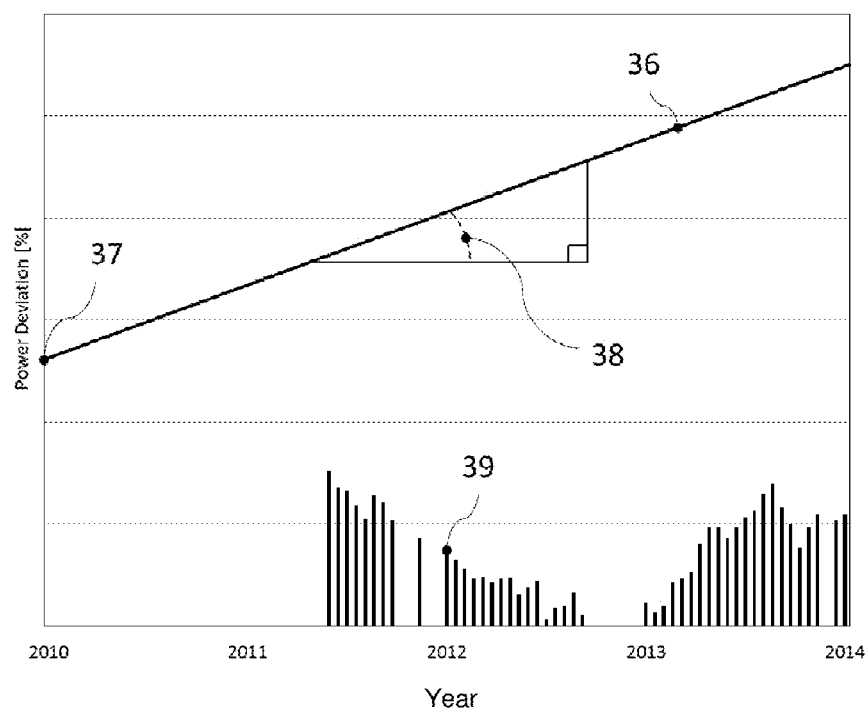
FIG. 15 shows a diagram of the module degradation and the rate of module soiling.

As shown in FIG. 15, the initial module degradation 37 is determined from the deviation of the module output power Deviation_P$_{Module}$ 36 and the point in time of startup of the power station 1. This is done according to the following formula.

$$D_{INITIAL}\ [\%] = \text{Deviation\_P}_{MODULE,Comm\_Date}$$

The inclination is now determined from the gradient of the curve 36, which corresponds to the annual module degradation rate 38. The annual module degradation rate 38 can be calculated as follows:

$$D_{ANNUAL}[\%/a] = \tan^{-1}\left(\frac{\text{Deviation\_P}_{MODULE,Today} - \text{Deviation\_P}_{MODULE,Comm\_Date}}{\text{Today} - \text{Comm\_Date [years]}}\right)$$

Finally, the degree of soiling 39 of the modules is determined through subtraction of the final deviations and deviation of the module output power Deviation_P$_{Module}$ 36 from the deviations and the deviation curve Deviation_P$_{LAST\ YEAR}$ 33. The following formula defines the degree of soiling accordingly.

$$\text{Soling [\%]} = \text{Deviation\_P}_{LAST\ YEAR} - \text{Deviation\_P}_{MODULE}$$

FIG. 15 shows the degree of soiling 39. The degree of soiling 39 is plotted for each valid day. On the basis of the degree or degrees of soiling, it is possible to establish a cleaning cycle for the power station 1, for example.

Individual steps of the method described above, such as the sensor normalization, for example, are optional. The sequence of the steps can also be altered. If possible, steps can also be carried out in parallel, or one step can be carried out implicitly in another step.

In accordance with the provisions of the patent statutes, the principle and mode of operation of this invention have been explained and illustrated in its preferred embodiments. However, it must be understood that this invention may be practiced otherwise than as specifically explained and illustrated without departing from its spirit or scope.

What is claimed is:

1. A method for detecting the degree of soiling of PV modules of a string, with the following steps:

determination of the deviations of the string power output values from a calculated reference value over the last year;

calculation of a historical trend line from the deviations;

determination of a maximum difference between the trend line and the deviations;

calculation of final deviations of the string power output values through subtraction of the maximum difference from the trend line; and determination of the degree of soiling through subtraction of the final deviations from the deviations.

2. The method as set forth in claim 1, wherein the method is based on daily values.

3. The method as set forth in claim 1, wherein an irradiation sensor is used for the calculation of the string power output values.

4. The method as set forth in claim 3, wherein a temporal mismatch of the string power output values as a result of alignment errors of the irradiation sensor is determined and considered.

5. The method as set forth in claim 3, wherein measurement errors as a result of the ageing of the irradiation sensor are determined by comparing all previously observed cloud-free days and considered.

6. The method as set forth in claim 1, wherein string power output values from a time interval around a maximum elevation angle of the sun are used.

7. The method as set forth in claim 1, wherein the string power output values are discarded if an output power of an inverter of the string exceeds a threshold, the threshold being greater than 95 percent and less than 100 percent of a rated output power of the inverter.

8. The method as set forth in claim 1, wherein the string power output values are discarded if an average measured radiation deviates from a simulated radiation by a threshold value, the threshold lying between 5 percent and 25 percent.

9. The method as set forth in claim 1, wherein the string power output values are discarded if a deviation between two temporally successive measured values of the radiation exceeds a threshold, the threshold lying between 100 watts per square meter and 300 W per square meter.

10. The method as set forth in claim 1, wherein the string power output values are discarded if an output power of an inverter of the string has been limited.

11. The method as set forth in claim 1, wherein an entire operating time of the PV modules is observed.

12. The method as set forth in claim 1, wherein the degree of soiling of at least one string is determined.

* * * * *